United States Patent

Sander et al.

Patent Number: 5,321,447
Date of Patent: Jun. 14, 1994

[54] OPHTHALMOSCOPIC ATTACHMENT FOR A SURGICAL MICROSCOPE

[75] Inventors: Ulrich Sander, Oberkochen; Fritz Strahle, Heubach-Lautern; Jurgen Liegel, Oberkochen, all of Fed. Rep. of Germany

[73] Assignee: Carl-Zeiss-Stiftung, Heidenheim/Brenz, Fed. Rep. of Germany

[21] Appl. No.: 875,634

[22] Filed: Apr. 28, 1992

[30] Foreign Application Priority Data

May 4, 1991 [DE] Fed. Rep. of Germany ....... 4114646

[51] Int. Cl.⁵ .......................... A61B 3/13; G02B 21/22
[52] U.S. Cl. ..................................... 351/216; 351/205; 351/220; 359/376; 359/381; 359/385
[58] Field of Search ......................... 351/205, 216, 220; 359/380, 381, 383, 384, 434, 785, 376, 377

[56] References Cited

U.S. PATENT DOCUMENTS

| | | | |
|---|---|---|---|
| 2,536,718 | 1/1951 | Brandon | 359/380 |
| 4,710,000 | 12/1987 | Spitznas et al. | 351/205 |
| 4,989,023 | 1/1991 | Sakurai et al. | 354/62 |
| 5,009,487 | 4/1991 | Reiner | 359/376 |

FOREIGN PATENT DOCUMENTS

| | | |
|---|---|---|
| 3539009 | 5/1987 | Fed. Rep. of Germany . |
| 8902035 | 5/1989 | Fed. Rep. of Germany . |
| 2005921 | 1/1990 | Japan . |
| 9115150 | 10/1991 | PCT Int'l Appl. . |
| 2005436 | 4/1979 | United Kingdom . |

*Primary Examiner*—Loha Ben
*Assistant Examiner*—Michael A. Papalas
*Attorney, Agent, or Firm*—Eugene Stephens & Associates

[57] ABSTRACT

An ophthalmoscopic attachment 1 for a surgical microscope 13 accommodates an optical system 14 which erects an inter-image of the fundus (or other particular area of the vitreous body of the eye) produced by at least one ophthalmoscopic lens 8 and interchanges the optical viewing paths. The optical system 14 is located directly behind the produced inter-image at a point where the stereoscopic optical viewing paths are still intertwined. The optical system 14 is configured either as a triplet with field lenses or as a straight-view inversion prism. The attachment also includes a lens 15 that is (a) positioned between the optical system 14 and the lens end of the attachment, and (b) movable along the optical axis of the attachment to put the critical section of the eye into focus.

13 Claims, 5 Drawing Sheets

OPHTHALMOSCOPIC ATTACHMENT FOR A SURGICAL MICROSCOPE

TECHNICAL FIELD

The invention herein relates to an ophthalmoscopic attachment for a stereo microscope for carrying out surgeries, particularly eye surgeries.

BACKGROUND

In known apparatus for viewing the fundus and other particular areas within the vitreous body of the human eye, an inter-image of the viewed part of the eye is generated by means of an ophthalmoscopic lens; and this inter-image is then viewed by means of a surgical microscope. The image viewed in this manner is inverted vertically and laterally, and is pseudo-stereoscopic, i.e., depth perception is inverted from front to back. However, in order to be able to perform microsurgery, it is necessary to provide an image that is stereoscopically correct, namely "right side up". In addition to this required image erection, the two viewed optical paths must be interchanged (pupil interchange) in order to prevent the occurrence of the pseudo-stereo effect which would otherwise occur during stereoscopic viewing.

Image erection and pupil interchange may be achieved by positioning a prism system between the binocular tubes and the magnification changers of the surgical microscope. Such a prism system is described, for example, in U.S. Pat. No. 4,710,000 (Spitznas et al.). This additional module increases the working distance between the eye of the patient and the pupil of the viewer. However, for ergonomic and practical reasons, such increased working distance is undesirable in medical applications. Furthermore, such a prism system becomes quite complex in those commonly occurring situations when a second binocular tube must be provided to accommodate another viewer. With this type of prior art prism system, the second viewing tube requires its own appropriate second such prism system.

German Patent Application No. 35 39 009 and German Utility Model No. G 89 02 035.9 suggest a second possible solution in which the ophthalmoscopic lens and an appropriate prism system for reversing the generated inter-image are accommodated in an attachment to the surgical microscope. In this second prior art solution, the image-reversing prism system is located directly in front of the main lens of the surgical microscope, and the area of the eye of interest is focused with the actual surgical microscope which has a two-element main lens, one main lens element being shifted relative to the other for such focusing purposes. Therefore, each time this prior art attachment is installed or interchanged, the surgical microscope must be refocused, which is quite a problem during surgery. This second prior art has another disadvantage: The inversion system is positioned directly in front of the main lens and spatially separates the diverging stereo beam paths completely at a point where these paths are still partially overlapping. As a result of this, portions of these two optical paths are partially blocked out, causing image errors (vignetting) in the surgical microscope. Such a system has a further disadvantage in that the surgical microscope must have greater length to include a two-element main lens, thereby reducing the possible operating range available for the surgeon's use.

International PCT Application WO 91/15150 describes a third prior art solution where means for inverting the image is placed directly behind the side of the ophthalmoscopic lens which faces the surgical microscope. The inversion system comprises several prisms. Since the inversion system is positioned directly behind the ophthalmoscopic lens, the inter-image produced by the ophthalmoscopic lens lies within the prisms and has to be observed there through the surgical microscope. Therefore, the prisms used for inverting the image must be made with extreme accuracy and without optical errors. This third solution has a further disadvantage, namely, focusing is made by either adjusting the whole device in a vertical direction or by moving one of the inverting prisms relative to the others, both of which focusing systems require relatively complex mechanical arrangements. Furthermore, when vertically adjusted, the distance between the patient's eye and the ophthalmoscopic lens does not remain constant but rather depends on the focusing adjustment.

Therefore, the problem to be solved by the present invention is to fulfill the need for a surgical microscope with an ophthalmoscopic attachment that provides a vertical inversion of an inter-image produced by an ophthalmoscopic lens and that interchanges the optical viewing paths, while permitting the optional use of a conventional surgical microscope, either in a conventional manner or as an ophthalmoscope, without requiring changes to the surgical microscope. In so doing, such a single ophthalmoscopic attachment must assure that an inter-image without image errors can be viewed stereoscopically through the surgical microscope, even by a second viewer, by merely the addition of another conventional binocular tube to the conventional microscope.

SUMMARY OF THE INVENTION

The ophthalmoscopic attachment of the invention herein accommodates an optical system which produces the desired image erection of the inter-image produced by an ophthalmoscopic lens or an ophthalmoscopic lens system in a first inter-image plane. In addition, the optical system interchanges the optical viewing paths (pupil interchange). The image erection and pupil interchange occur directly behind the first inter-image plane at a point where the stereoscopic optical viewing paths do not yet run completely separately, but rather are still intertwined with each other. The erect, unreversed image may then be viewed stereoscopically correct with the conventional surgical microscope without requiring any additional adjustments of the surgical microscope.

Furthermore, our attachment accommodates a focusing lens between its image-reversing/erecting optical system and the lens end of the attachment. This focusing lens may be moved along the optical axis to focus on the particular area of the eye being viewed. In so doing, the focus is adjusted on the inventive attachment without requiring adjustment of the conventional surgical microscope.

The viewing mode through the surgical microscope, i.e., use of the surgical microscope with or without the ophthalmoscopic attachment, may be changed rapidly by the operator without requiring time-consuming focus adjustments on the surgical microscope each time the viewing mode is changed. With the use of an appropriate pivoting mechanism for the inventive attachment, the viewing mode may be changed rapidly.

Therefore, the operating distance between the patient's eye and the viewer's eye remains constant even though the inventive attachment may be moved into or out of its operative position. Therefore, our attachment can be optionally used with any conventional surgical microscope; and even if the conventional microscope accommodates additional viewers by means of additional binocular tubes sharing the microscope's one main lens, no supplement to our single attachment is required. Image erection and pupil interchange are effected either by an optical system which consists of two field lenses and a triplet, or by a straight-view inversion prism (or an equivalent mirror arrangement) located in the inventive attachment.

DRAWINGS

DETAILED DESCRIPTION OF PREFERRED EMBODIMENTS

Figure 1:
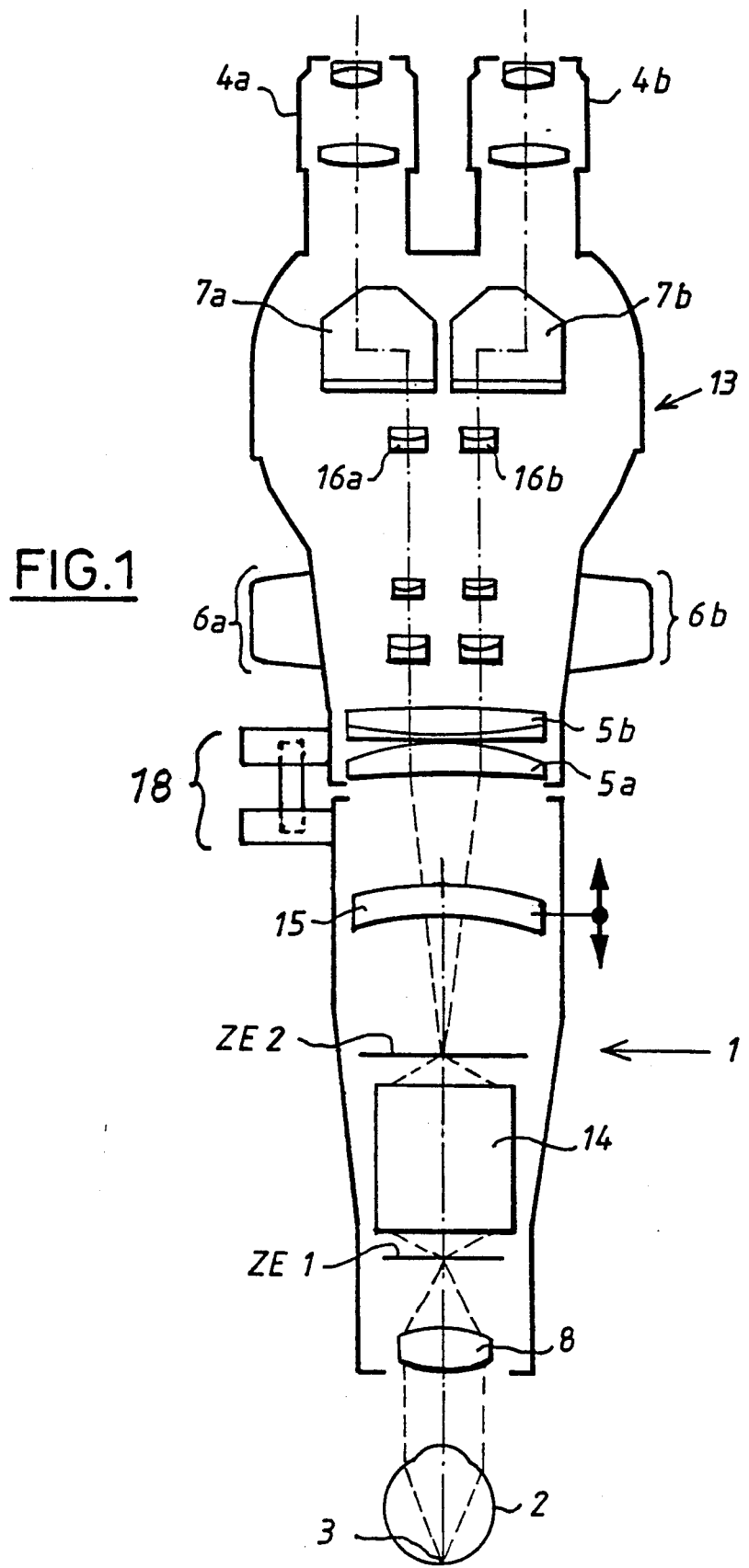
FIG. 1 is a schematic diagram of a conventional surgical microscope in combination with the inventive ophthalmoscopic attachment, showing the optical system for image erection and pupil interchange as a lens system in block form.

FIG. 1 shows, in combination, a surgical microscope 13 with a main lens 5a, 5b and the inventive ophthalmoscopic attachment 1 accommodating an optical system 14 for image erection and pupil interchange. Ophthalmoscopic attachment 1 has, on its end facing a patient's eye 2, an ophthalmoscopic lens 8 which produces a vertically and laterally inverted image of the viewed fundus 3, in a first inter-image plane ZE1. By means of the adjoining optical system 14 (in this embodiment, a lens arrangement), the image is erected and projected unreversed in a second inter-image plane ZE2. The image in said inter-image plane ZE2 is viewed through conventional surgical microscope 13 which is constructed in a well-known manner. Hence, the magnification controls 6a, 6b, as well as the tube lenses 16a, 16b and the inversion prisms 7a, 7b for the two separate optical paths, are located behind one main lens 5a, 5b. Stereoscopic viewing takes place through the binocular tubes 4a, 4b. The use of one main lens 5a, 5b for both optical viewing paths is not specific to the present invention. It is also possible to provide a separate lens for each of the two optical viewing paths.

A lens 15 is mounted between optical system 14 and the lens end of the attachment 1 (which faces microscope 13) so that lens 15 can be moved along the optical axis. By moving lens 15, it is possible to focus on any particular area of the vitreous body of the eye 2 without requiring a change of surgical microscope 13. Further, a pivoting means 18 makes it possible to use the surgical microscope optionally in a conventional manner, selectively positioning ophthalmoscopic attachment 1 in front of main lens 5a, 5b when appropriate for eye surgery.

Figure 2:
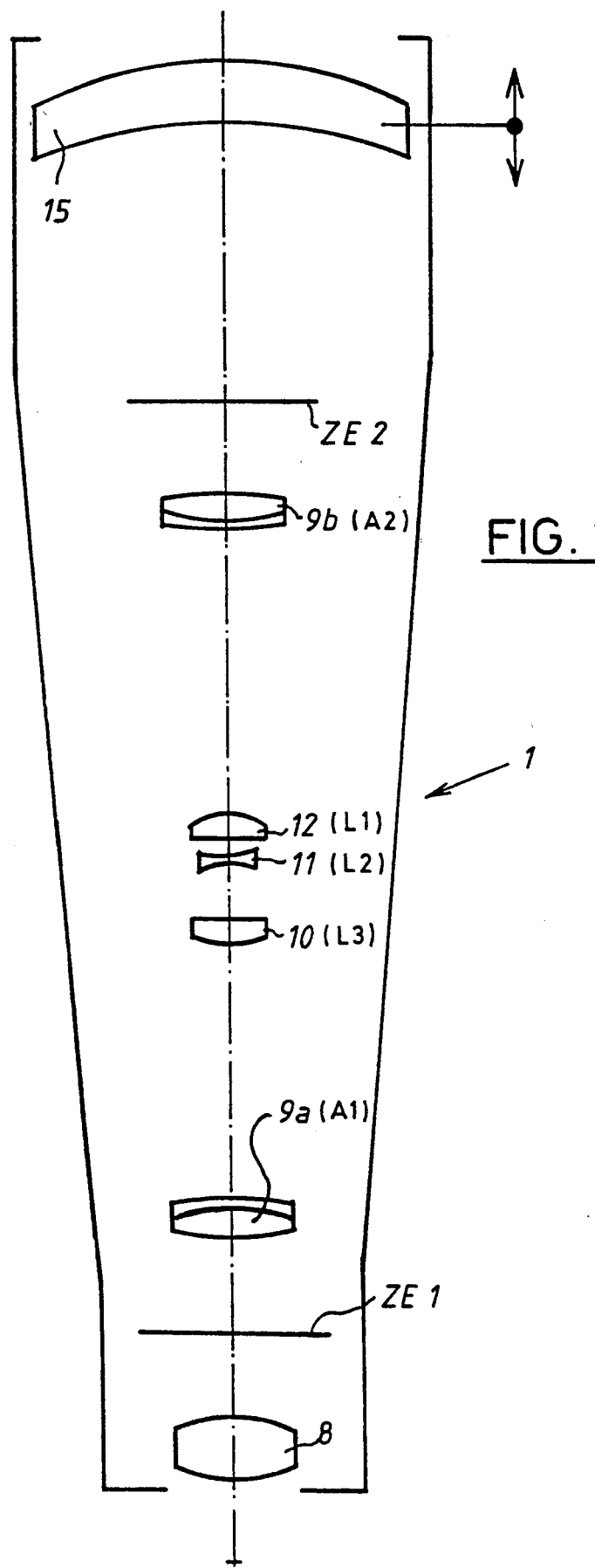
FIG. 2 is an enlarged schematic diagram of only the inventive ophthalmoscopic attachment of FIG. 1, showing the lens system in greater detail.

FIG. 2 is an enlarged view of ophthalmoscopic attachment 1 of FIG. 1 in which the optical system for image erection and pupil interchange consists of a lens system with several lenses 9a, 10, 11, 12, 9b. Ophthalmoscopic lens 8, which is located on the side of the attachment 1 facing the patient's eye, produces in inter-image plane ZE1 a vertically and laterally reversed image of the viewed part of the eye. This image is erected on a scale of 1:1 by the subsequent five lenses 9a, 10, 11, 12, 9b and is projected unreversed in inter-image plane ZE2. The actual image formation occurs by means of a triplet which comprises two lenses exhibiting positive refractive power (L3:10, L1:12) and one interposed lens exhibiting negative refractive power (L2:11). Two additional compound lenses A1:9a, A2:9b act as field lenses. Lens 15 is moved along the optical axis inside attachment 1 whereby the critical section of the eye is put into focus. The image produced in the inter-image plane ZE2 is viewed with surgical microscope 13.

It should be understood that the optical projection path of the just-described lens system can be appropriately deflected in a nonlinear manner in order to be able to accommodate the individual elements in a dimensionally shorter attachment housing.

In an embodiment of this lens system which consists of a triplet $L1:f_1$, $L2:f_2$, $L3:f_3$ and two field lenses $A1:9a$, $A2:9b$ and which has been color-corrected for the wavelength ranges of 436 nm, 480 nm, 546 nm, and 644 nm in the visible spectral region, the focal length ratios which can be realized with a surgical microscope having a focal length of the main lens of 200 mm are within the following ranges:

$$f_3:f_1 = [0.9 \ldots 2.0]$$

$$-f_2:f_1 = [0.4 \ldots 0.6]$$

Within these ranges, an acceptable length of the ophthalmoscopic attachment can be attained, thereby offering a large operating area beneath the surgical microscope. In addition, the optical system assures a high-quality image.

Figure 3:
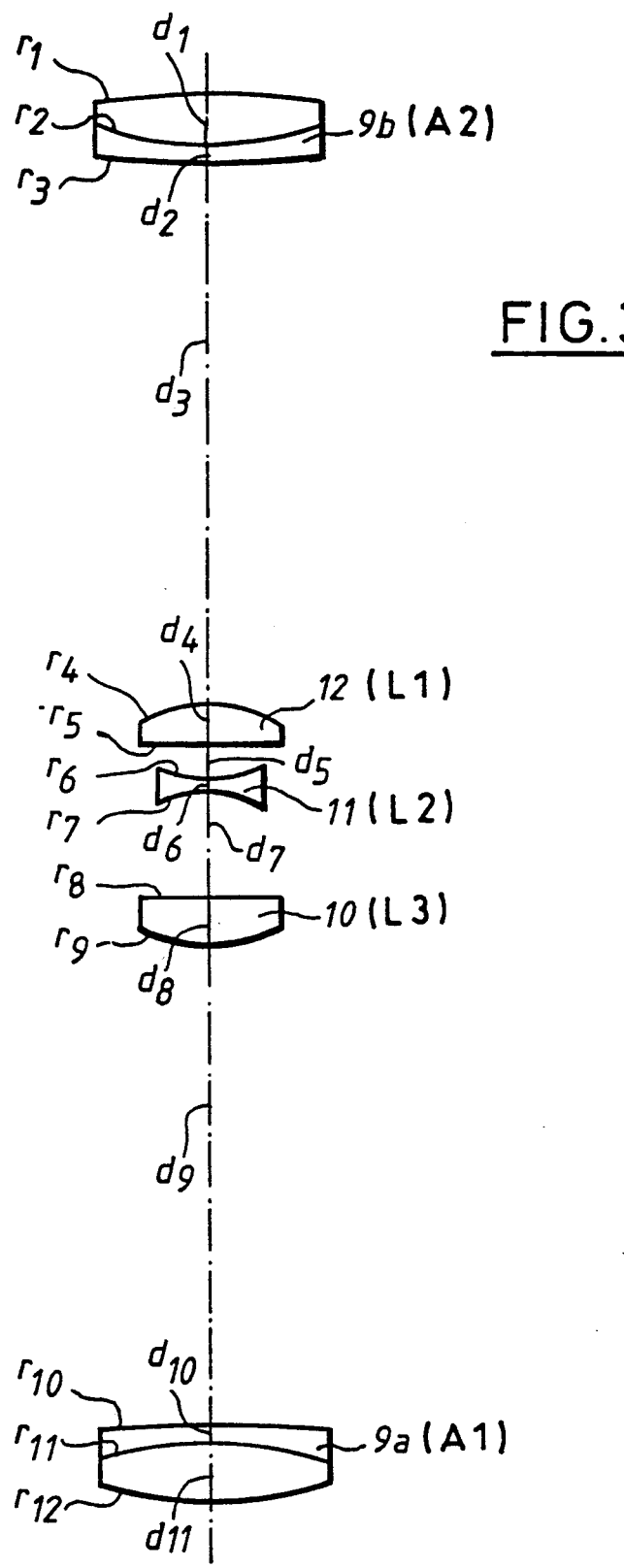
FIG. 3 is a farther enlarged and more detailed schematic view of the lens system of FIG. 2, identifying relevant lens radii, lens thicknesses, and lens distances.

FIG. 3 shows an enlarged view of the optical system of FIG. 2 identifying the lens radii $r_i$, lens thicknesses $d_i$, and lens distances $d_i$, as used in the data sets of the tables specified in the claims. Of course, comparably good imaging results may also be obtained with some variation of the individual parameters of these preferred data sets.

Figure 4:
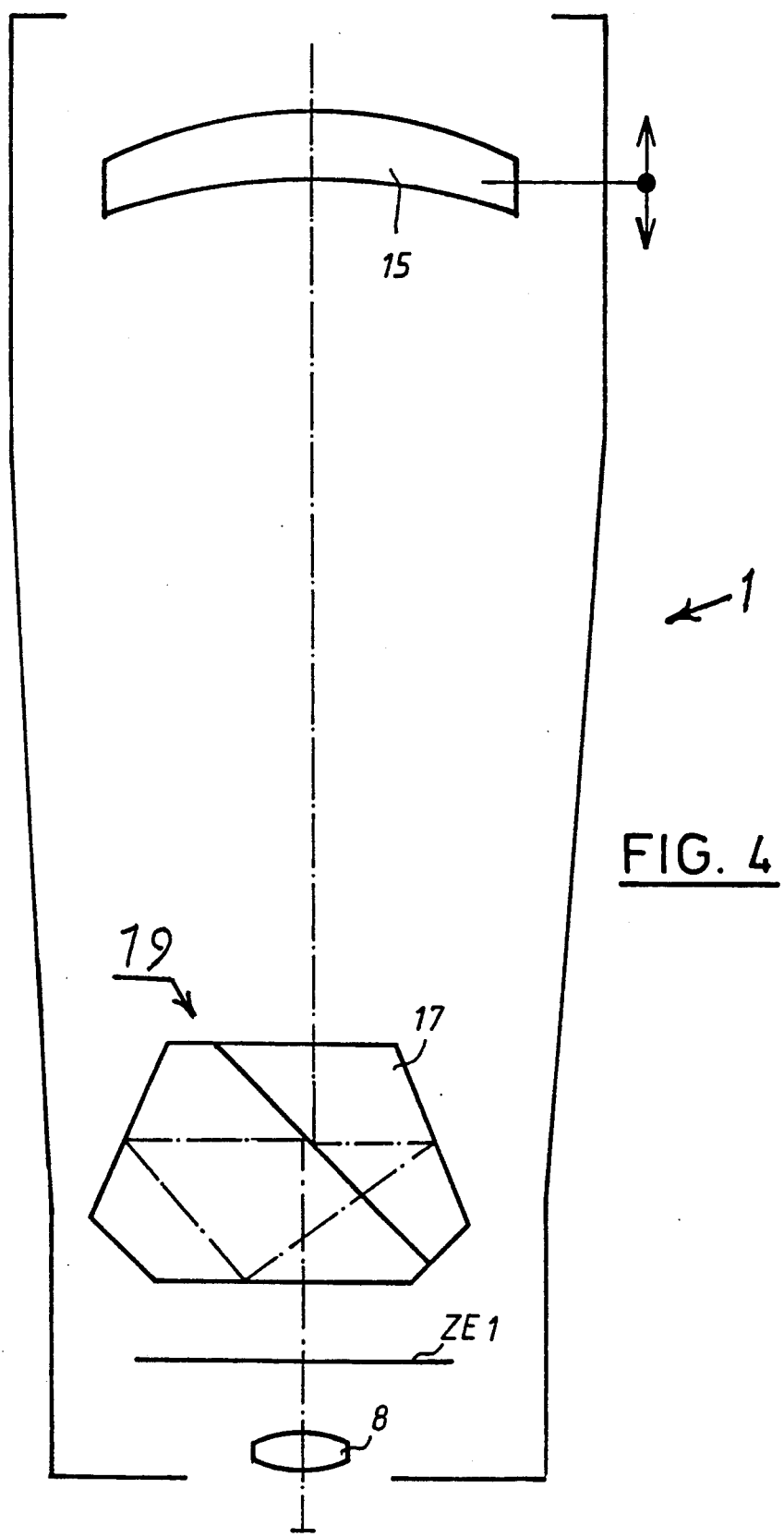
FIG. 4 is a schematic diagram of a second embodiment of the inventive ophthalmoscopic attachment in which the optical system for image erection and pupil interchange is a straight-view inversion prism.

FIG. 4 shows a second preferred embodiment of the inventive attachment 1 which accommodates a reflection-path optical system 19 directly behind the first inter-image plane ZE1. Optical system 19 is configured as either a straight-view inversion prism or as a mirror system exhibiting the same illustrated function wherein the inter-image of the fundus, or some other selected area within the vitreous body of the eye, is erected and the optical viewing paths are interchanged. Preferably, optical system 19 is a straight-view Schmidt-Pechan prism having a roof 17.

It should be noted that the positioning of reflection-path optical system 19 at the point where the stereoscopic optical paths are still intertwined permits a very compact construction for the inversion prism or the mirror system and for attachment 1, because the total optical path exhibits its smallest radial expansion at this point. Furthermore, focusing lens 15 is accommodated between inversion prism 19 and the lens end of attachment 1, lens 15 being moved along the optical axis for focusing the critical section of the eye.

Figure 5:
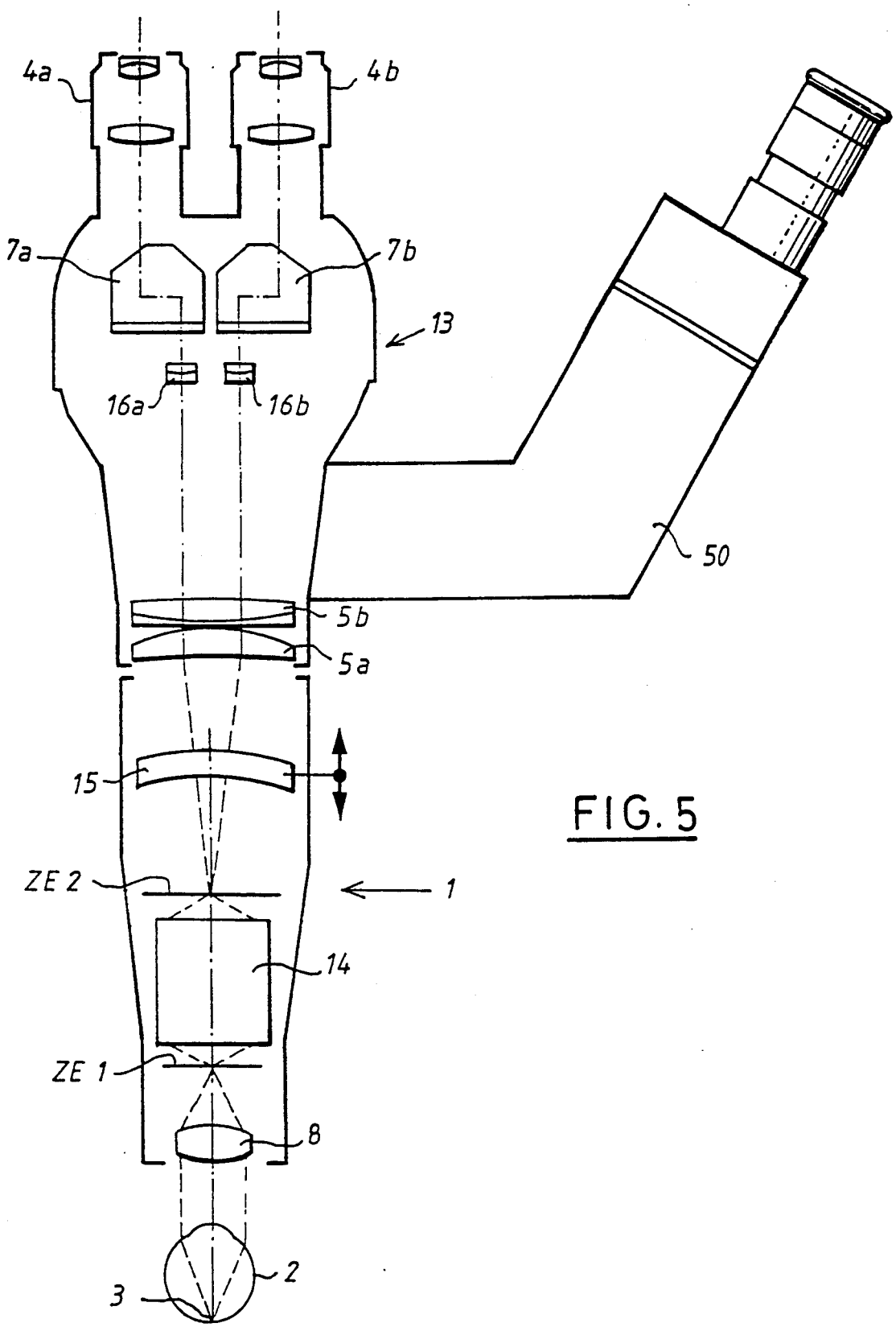
FIG. 5 is a schematic diagram of a conventional surgical microscope in combination with the inventive ophthalmoscopic attachment, showing the optical system for image erection and pupil interchange as a lens system in block form, the microscope including a second conventional binocular tube for use by a second viewer.

As indicated above, our inventive ophthalmoscopic attachment can be optionally used with any conventional surgical microscope; and even if the conventional microscope accommodates additional viewers by means of an additional binocular tube 50 (FIG. 5) with a second pair of stereoscopic optical viewing paths sharing the microscope's one main lens 5a, 5b, no supplement to our single attachment is required.

We claim:

1. An ophthalmoscopic attachment for a surgical microscope for viewing the fundus or other particular area of the vitreous body of the eye, said microscope having a main lens and at least one pair of stereoscopic optical viewing paths that are spacially separated behind said main lens, said attachment comprising:
   an optical axis extending from an eye-facing end to a lens end which faces the microscope;
   at least one ophthalmoscopic lens positioned in proximity to said eye-facing end for producing an inter-image of said area of the eye on an inter-image plane;
   optical system means for erecting said inter-image and for interchanging said optical viewing paths, said optical system means being located directly behind said inter-image plane where said stereoscopic optical viewing paths are still intertwined and are not yet spacially separated; and
   lens means, movable along said optical axis and positioned between said optical system means and said lens end, for adjusting the focus of said particular area of the eye being viewed.

2. The ophthalmoscopic attachment of claim 1 further comprising pivot means for connecting said attachment to said surgical microscope so that said attachment may be selectively positioned in front of said main lens.

3. The ophthalmoscopic attachment of claim 1 wherein said optical system means is a lens system in which a triplet is positioned between two field lenses, said triplet comprising one lens displaying negative refractive power interposed between two lenses displaying positive refractive power.

4. The ophthalmoscopic attachment of claim 3 wherein said optical system means produces an image of said inter-image produced by said ophthalmoscopic lens at an object-to-image ratio of 1:1.

5. The ophthalmoscopic attachment of claim 4 wherein:
   said main lens of the surgical microscope has a focal length of 200 mm;
   said two field lenses and triplet comprising said lens system are color-error-corrected; and
   in said triplet, the focal lengths $f_1$ and $f_3$ of said two lenses displaying positive refractive power and the focal length $f_2$ of said one lens displaying negative refractive power have focal length ratios within the following ranges:

$$f_3 : f_1 = [0.9 \ldots 2.0]$$

$$-f_2 : f_1 = [0.4 \ldots 0.6].$$

6. The ophthalmoscopic attachment of claim 5 further comprising a predetermined lens system design wherein $f_3 : f_1 = 2.0$ and $-f_2 : f_1 = 0.545$, and wherein the characteristics of the lens elements and their spatial relationship to each other are substantially in the proportions indicated by the data in the following table, the radii of the respective surfaces being designated by r with a numerical subscript identifying the particular surface numbered consecutively from said lens end, the thickness and spacings being designated by d with a numerical subscript numbered in a single series from said lens end, and the respective indices of refraction n and the Abbe numbers $v_e$ of the elements being given in the indicated columns:

| Lens | Radius $r_i$/mm | Thickness $d_i$/mm | Distance $d_i$/mm | Refractive Index n(546 nm) | Abbe Number $v_e$ |
|---|---|---|---|---|---|
|    | $r_1 = 4.9911$ | | | | |
|    |                | $d_1 = 3.000$ | | 1.68637 | 44.2 |
| A2 | $r_2 = -18.9821$ | | | | |
|    |                  | $d_2 = 1.000$ | | 1.81265 | 25.2 |
|    | $r_3 = -59.2871$ | | | | |
|    |                  | | $d_3 = 30.750$ | | |
|    | $r_4 = 6.4576$ | | | | |
| L1 |                | $d_4 = 2.500$ | | 1.80730 | 46.1 |
|    | $r_5 = -140.0550$ | | | | |
|    |                   | | $d_5 = 1.948$ | | |
|    | $r_6 = -8.7323$ | | | | |
| L2 |                 | $d_6 = 0.600$ | | 1.81265 | 25.2 |
|    | $r_7 = 5.7935$ | | | | |
|    |                | | $d_7 = 6.175$ | | |
|    | $r_8 = 925.3580$ | | | | |
| L3 |                  | $d_8 = 2.500$ | | 1.80730 | 46.1 |
|    | $r_9 = -12.3903$ | | | | |
|    |                  | | $d_9 = 27.530$ | | |
|    | $r_{10} = 86.8200$ | | | | |
|    |                    | $d_{10} = 1.000$ | | 1.81265 | 25.2 |
| A1 | $r_{11} = 17.1400$ | | | | |
|    |                    | $d_{11} = 3.000$ | | 1.68637 | 44.2 |
|    | $r_{12} = -31.4353$ | | | | |

7. The ophthalmoscopic attachment of claim 5 further comprising a predetermined lens system design wherein $f_3:f_1=1.66$ and $-f_2:f_1=0.56$, and wherein the characteristics of the lens elements and their spatial relationship to each other are substantially in the proportions indicated by the data in the following table, the radii of the respective surfaces being designated by r with a numerical subscript identifying the particular surface numbered consecutively from said lens end, the thickness and spacings being designated by d with a numerical subscript numbered in a single series from said lens end, and the respective indices of refraction n and the Abbe numbers $v_e$ of the elements being given in the indicated columns:

| Lens | Radius $r_i$/mm | Thickness $d_i$/mm | Distance $d_i$/mm | Refractive Index n(546 nm) | Abbe Number $v_e$ |
|---|---|---|---|---|---|
| A2 | $r_1 = 30.5000$ | $d_1 = 3.000$ | | 1.68637 | 44.2 |
|  | $r_2 = -18.9820$ | $d_2 = 1.000$ | | 1.81265 | 25.2 |
|  | $r_3 = -59.2870$ | | $d_3 = 31.687$ | | |
| L1 | $r_4 = 5.9576$ | $d_4 = 2.500$ | | 1.61521 | 58.4 |
|  | $r_5 = 50.5546$ | | $d_5 = 3.277$ | | |
| L2 | $r_6 = -6.0844$ | $d_6 = 1.000$ | | 1.65222 | 33.6 |
|  | $r_7 = 5.4845$ | | $d_7 = 2.333$ | | |
| L3 | $r_8 = 17.7756$ | $d_8 = 2.500$ | | 1.61521 | 58.4 |
|  | $r_9 = -8.1069$ | | $d_9 = 23.117$ | | |
| A1 | $r_{10} = 86.8200$ | $d_{10} = 1.000$ | | 1.81265 | 25.2 |
|  | $r_{11} = 17.1400$ | $d_{11} = 3.000$ | | 1.68637 | 44.2 |
|  | $r_{12} = -30.5299$ | | | | |

8. The ophthalmoscopic attachment of claim 5 further comprising a predetermined lens system design wherein $f_3:f_1=0.88$ and $-f_2:f_1=0.40$, and wherein the characteristics of the lens elements and their spatial relationship to each other are substantially in the proportions indicated by the data in the following table, the radii of the respective surfaces being designated by r with a numerical subscript identifying the particular surface numbered consecutively from said lens end, the thickness and spacings being designated by d with a numerical subscript numbered in a single series from said lens end, and the respective indices of refraction n and the Abbe numbers $v_e$ of the elements being given in the indicated columns:

| Lens | Radius $r_i$/mm | Thickness $d_i$/mm | Distance $d_i$/mm | Refractive Index n(546 nm) | Abbe Number $v_e$ |
|---|---|---|---|---|---|
| A2 | $r_1 = 42.9911$ | $d_1 = 1.696$ | | 1.68637 | 44.2 |
|  | $r_2 = -18.9821$ | $d_2 = 0.848$ | | 1.81265 | 25.2 |
|  | $r_3 = -59.2871$ | | $d_3 = 32.070$ | | |
| L1 | $r_4 = 7.9988$ | $d_4 = 2.500$ | | 1.80730 | 46.1 |
|  | $r_5 = -106.2270$ | | $d_5 = 2.620$ | | |
| L2 | $r_6 = -9.5154$ | $d_6 = 0.600$ | | 1.81265 | 25.2 |
|  | $r_7 = 7.7269$ | | $d_7 = 4.940$ | | |
| L3 | $r_8 = -148.7780$ | $d_8 = 2.500$ | | 1.80730 | 46.1 |
|  | $r_9 = -11.5635$ | | $d_9 = 28.490$ | | |
| A1 | $r_{10} = 86.8223$ | $d_{10} = 0.848$ | | 1.81265 | 25.2 |
|  | $r_{11} = 17.1339$ | $d_{11} = 1.696$ | | 1.68637 | 44.2 |
|  | $r_{12} = -28.2267$ | | | | |

9. The ophthalmoscopic attachment of claim 1 wherein said optical system means is a reflection-path optical system comprising one of (a) a straight-view inversion prism system and (b) a mirror system exhibiting the same beam path.

10. The ophthalmoscopic attachment of claim 9 wherein said straight-view inversion prism system is a Schmidt-Pechan prism having a roof.

11. The ophthalmoscopic attachment of claim 1 wherein said surgical microscope has a second pair of stereoscopic optical viewing paths for observing said particular area of the eye being viewed.

12. An ophthalmoscopic attachment for a surgical microscope for viewing the fundus or other particular area of the vitreous body of the eye, said microscope having a main lens and at least one pair of spacially-separated stereoscopic optical viewing paths that are positioned behind said main lens, said attachment comprising:

an optical axis extending from an eye-facing end to a lens end which faces the microscope;

at least one ophthalmoscopic lens positioned in proximity to said eye-facing end for producing an inter-image of said area of the eye on a first inter-image plane;

a lens system positioned directly behind said first inter-image plane, where said stereoscopic optical viewing paths are still intertwined and are not yet spacially separated, so that said lens system (a) erects said inter-image, (b) interchanges said optical viewing paths, and (c) projects said erected and unreversed image on a second image plane which is viewed through said microscope; and lens means, movable along said optical axis and positioned between said lens system and said lens end, for adjusting the focus of said particular area of the eye being viewed.

13. The ophthalmoscopic attachment of claim 12 wherein said lens system comprises a triplet in which one lens displaying negative refractive power is interposed between two lenses displaying positive refractive power.

* * * * *